United States Patent [19]

Burdett

[11] 4,391,919

[45] Jul. 5, 1983

[54] ALCOHOL SEPARATION PROCESS

[75] Inventor: Ian D. Burdett, Charleston, W. Va.

[73] Assignee: Union Carbide Corporation, Danbury, Conn.

[21] Appl. No.: 279,098

[22] Filed: Jun. 30, 1981

[51] Int. Cl.³ .................... C07C 27/06; C07C 27/34
[52] U.S. Cl. .................................. 518/725; 518/700; 518/701
[58] Field of Search ............... 518/728, 700, 701, 725; 568/918

[56] References Cited

U.S. PATENT DOCUMENTS

| | | | |
|---|---|---|---|
| 2,116,665 | 5/1938 | Brown | 195/2 |
| 2,313,196 | 3/1943 | Guinot | 260/643 |
| 2,325,783 | 8/1943 | Lorand | 260/637 |
| 2,444,296 | 6/1948 | Keim et al. | 260/637 |
| 2,461,220 | 2/1949 | Lorand | 260/637 |
| 2,558,556 | 6/1951 | Hess et al. | 260/450 |
| 2,571,151 | 10/1951 | McGrath et al. | 260/450 |
| 2,581,712 | 1/1952 | Rottig et al. | 260/450 |
| 2,583,620 | 1/1952 | Wrightson | 260/450 |
| 2,658,069 | 11/1953 | Van der Waals | 260/450 |
| 2,664,435 | 12/1953 | Burton et al. | 260/450 |
| 2,675,401 | 4/1954 | Laemmle et al. | 260/450 |
| 2,918,486 | 12/1959 | Binning et al. | 260/450 |
| 2,979,520 | 4/1961 | Kenton | 260/450 |
| 3,391,190 | 7/1968 | Kilsheimer et al. | 260/586 |
| 4,001,289 | 1/1977 | Dougherty et al. | 260/450 |
| 4,038,329 | 7/1977 | Palmer et al. | 260/637 P |
| 4,228,094 | 10/1980 | Bryant | 260/450 |
| 4,263,218 | 4/1981 | Dougherty | 260/450 |

Primary Examiner—Howard T. Mars
Attorney, Agent, or Firm—Norman L. Balmer

[57] ABSTRACT

The process involves the separation of monohydric and polyhydric products from a liquid homogeneous mixture obtained from the reaction of hydrogen and oxides of carbon in a solvent solution containing a Group VIII metal carbonyl complex catalyst by extracting said solvent solution with a liquid polyhydric alcohol having at least four carbon atoms and at least four hydroxyl moieties at a temperature of at least 50° C. Further, the process is advantageous in that it can be effected under pressure in the presence of oxides of carbon.

13 Claims, No Drawings

ALCOHOL SEPARATION PROCESS

BACKGROUND OF THE INVENTION

This invention relates to the recovery of monohydric and polyhydric alcohol products from a homogeneous liquid phase mixture containing a Group VIII metal complex, etheral and/or other organic solvents and organic or inorganic promoters. More particularly, this invention relates to the separation of these alcohol products of the reaction between oxides of carbon and hydrogen in a homogeneous liquid phase reaction containing a Group VIII metal carbonyl complex from the homogeneous liquid phase.

There are described in U.S. Pat. Nos. 3,833,634 and 3,957,857, for example, processes involving the high pressure reaction of oxides of carbon and hydrogen in the presence of a rhodium carbonyl complex catalyst to produce, as the most preferred products, polyhydric alcohols such as ethylene glycol and 1,2-propylene glycol. It has been pointed out in U.S. Pat. No. 3,957,875 that a preferred rhodium carbonyl complex catalyst is a rhodium carbonyl cluster. The nature of that catalyst under the conditions of the reaction or as it is provided to the reaction can be characterized by its infrared spectrum. However, such catalysts frequently take another structure at temperatures and pressures lower than those used in the reaction.

In a preferred embodiment of those processes, the reaction is conducted in a homogeneous liquid phase mixture, so that the catalyst and the alcohol products formed from the reaction are in solution. The solution typically requires the presence of a production solvent mainly to keep the catalyst in solution before and after the reaction. The main, and most valuable, products of those processes are high boiling alkane polyols such as ethylene glycol and the secondary, and less valuable, although nonetheless valuable, products are lower boiling monohydric products such as methanol, etc. These products are generally removed by distillation, but in a continuous process rather severe changes in temperature and pressure would be required from the conditions employed in the high pressure reaction to the conditions employed in separation of the product. The rhodium catalyst in these processes is extremely expensive and very sensitive to temperature and pressure such that, generally, an increase of temperature and decrease in pressure result in an increase in the amount of rhodium catalyst which precipitates from the production solvent. Accordingly, any process for the recovery of the products by an extraction process must take into account the necessity of minimizing the loss of rhodium catalyst from or deactivation of the rhodium catalyst in the production solvent.

However, rhodium carbonyl complexes vary in structure based upon the temperature, solvent, promoter, salt, and carbon monoxide and hydrogen pressure imposed upon them. Therefore, a catalyst complex which may be extremely stable in a solution at one temperature such as during the reaction, could precipitate out of the solution at another temperature such as used during product recovery by distillation or other means.

In the case of large scale processes, significant catalyst losses are unacceptable. In the case of the processes of the U.S. patents referred to, catalyst losses in the order of, for example, about 0.1 percent by weight of the rhodium content on a per pass basis would in all likelihood make the process uneconomical. This can be better appreciated when one realizes the high current price for rhodium metal. Thus, in the commercial practice of these processes it will be necessary to avoid loss of an amount of rhodium metal which causes the cost of product(s) produced to be greater than cost of the same product(s) produced by other competitive processes.

U.S. Pat. No. 4,001,289 issued Jan. 4, 1977 described the separation of alcohol products from a liquid phase homogeneous mixture (the production solution) obtained from the reaction of oxides of carbon and hydrogen in a solvent solution containing a rhodium carbonyl complex catalyst in a manner which minimizes catalyst instability. This is accomplished by mixing the mixture with water and an essentially water immiscible organic extraction solvent for the rhodium complex present in the mixture, forming a water phase containing the alcohol product and an organic solvent phase containing all of the rhodium complex, and separating the phases to effect recovery of product from the water phase without effecting significant catalyst losses since the water phase is essentially free of the rhodium.

Similarly, processes employing Group VIII metal catalysts other than rhodium, are disclosed in U.S. Pat. Nos. 2,535,060, 2,636,046, and 2,549,470. In particular, these patents disclose processes wherein ruthenium catalysts, as well as other Group VIII metal catalyst, may be employed. The instant process is applicable to such process and is particularly applicable to processes wherein a ruthenium catalyst is employed.

In U.S. Pat. No. 4,228,094 there is disclosed an ethylene glycol recovery process to extract ethylene glycol and glycerine directly from tetraglyme and tetraglyme/sulfolane mixtures using glycerine as the extraction solvent. Owing to the high viscosity of the glycerine it was necessary to use a centrifugal extractor to achieve sufficient phase contact between the extraction solvent and the production solvent. The recovery of ethylene glycol (solvent to feed ratios of about 1:1 wt. ratio) were about 80 percent to 95 percent but solvent crossover of about 15 percent to about 25 percent occured, especially with the mixed solvent system. The amount of glycerine in the production solvent after the extraction can be reduced by use of a cooled decanter. Rhodium transfer to the extraction solvent was observed (50 ppm). An improvement in the process of U.S. Pat. No. 4,001,289 is described in U.S. Pat. No. 4,263,218 wherein the recovery of alcohol products produced by these rhodium complex catalyzed phase homogeneous mixtures in contact with CO gas.

The improved process of this invention involves the separation of alcohol products from a liquid phase homogeneous mixture obtained from the reaction of oxides of carbon and hydrogen in a solvent solution containing a Group VIII metal, particularly a rhodium metal catalyst, by mixing the liquid phase homogeneous mixture with a liquid polyhydric alcohol having at least four carbons and at least four hydroxyl groups, hereinafter extraction solvent, said mixture of the liquid phase homogenous mixture and polyhydric alcohol having a temperature of at least about 50° C. so to form an extraction solvent phase containing alcohol product and a liquid homogenous mixture phase containing the greater concentration of the rhodium. Concentrations of the Group VIII metal (e.g., rhodium) in the extraction solvent of less than 50 ppm have been observed with as low as about 5 ppm and less being attainable.

The instant process is carried out at a temperature of at least 50° C. and preferably about 50° C. to about 450° C. at which temperature the rhodium catalyst has little tendency to transfer into the extraction solvent thus permitting recycling of the production solvent to the reactor with a greater concentration of the rhodium catalyst contained therein than in the extraction solvent. The selectivity of the extraction solvent for the products over that of the production solvent provide for the determination of the extraction solvent flow which can be small (50 percent to about 125 percent of the production solvent flow) and therefore, the cross-section and number of contacting sections in the extraction zone can be relatively small. Further, the instant process may be carried out at process pressures, i.e. the high pressures employed in the process to form the products. This is an important advantage since the cost involved in recompressing the gas which is released from the production solvent when decompressed is a considerable fraction of the cost of carrying out the process.

The term "admixing" or "admixture" as used below, means a physical touching of the production solvent and the extraction solvent. In addition, a CO-containing gas may be present as illustrated by providing the gas at the surface of the mixture, or bubbling the gas through the mixture, and the like, when the admixing of the liquid phase homogeneous mixture (i.e., the "production solution") and the extraction solvent is in contact with CO-containing gas.

The typical production solution (i.e., "liquid phase homogeneous mixture") which is to be treated in accordance with this invention will contain the "product(s)" of the reaction, such as the alcohols: ethylene glycol, methanol, ethanol, propanol; esters: ethylene glycol monoformate, methyl formate, ethyl formate; and the like; the catalyst in the form of a Group VIII metal catalyst and a production solvent for the catalyst which is also compatible with the products of the reaction. The amount of product in the solution can vary greatly, from about 1 to about 75 weight percent of the solution. The production solvent can be present in a broad range, such as from about 25 to about 99 weight percent of the solution. The catalyst concentration can vary greatly, from about $1 \times 10^{-6}$ weight percent, or even less, to about 30 weight percent, or more, based on its Group VIII metal content. The composition of the liquid homogeneous mixture being treated according to this invention is not narrowly critical. All that is required in the solution (or mixture) is any amount of reaction product which is to be recovered, and any amount of a Group VIII metal catalysts solvated by a production solvent.

The Group VIII metal catalyst present in the production solution does not have to have the structure of the metal carbonyl complex. All that is required for the process of this invention is that the Group VIII metal values, as a complex, employed in the reaction, be in solution.

The solubilization of the Group VIII metal complex is typically dependent upon the production solvent used to effect the homogeneous mixture. The desired solvent is any liquid material which dissolves or keeps in solution the components of the homogeneous mixture taken from the reactor. It must be solution compatible with the reaction products and the Group VIII metal complex.

The Group VIII metals employed herein may be platinum, palladium, rhodium, ruthenium, cobalt, nickel, osmium, iron, and iridium. The preferred Group VIII metals are rhodium and ruthenium. The actual form of the Group VIII metal employed herein is of little importance so long as the Group VIII metal catalyst is solubilized in the production solvent used to effect the homogeneous mixture.

Illustrative production solvents which are generally believed to be suitable in making the homogeneous mixture (i.e., the production mixture) include, for example, ethers such as tetrahydrofuran, tetrahydropyran, diethyl ether, 1,2-dimethoxybenzene, 1,2-diethoxybenzene, the mono- and dialkyl ethers of ethylene glycol, of propylene glycol, of butylene glycol, of diethylene glycol, of dipropylene glycol, of triethylene glycol, of tetraethylene glycol, of dibutylene glycol, of oxethylene-propylene glycol, etc.; gamma-butyrolactone, deltavalerolactone; substituted and unsubstituted tetrahydrothiophene-1,1-dioxides (sulfolanes) as disclosed in U.S. Pat. No. 4,224,237, issued Sept. 23, 1980, the disclosure at pages 6 and 7 of the specification of which is incorporated herein by reference. The aforementioned solvents may not all provide the same degree separation of the monohydric and polyhydric products when employed as the solvent for the homogeneous mixture used in the instant process since such necessarily depends on a number of factors, e.g., temperature, pressure, promoter, etc.

Also, the crown ethers are suitable herein, particularly those as described in U.S. Pat. No. 4,162,261, issued July 24, 1979, which application is incorporated herein by reference. The crown ethers described therein contain at least four oxygen heteroatoms and include [18]-crown-6 and [15]-crown-5.

Particularly, it is believed that desirable production solvents are tetraglyme, sulfolane, gamma-butyrolactone and the crown ethers. Other very desirable solvents include mixtures of tetraglyme and sulfolane, mixtures of sulfolane and butyrolactne, mixtures of crown ethers and sulfolane, mixtures of crown ethers and tetraglyme, mixtures of crown ethers and butyrolactone, and mixtures of tetraglyme and butyrolactone.

A number of nitrogen containing bases and additionally salts, may be associated with the rhodium carbonyl complex in the homogeneous mixture. They are used to promote the catalyst's activity in the course of reaction. The kinds of each which may be selected is dependent upon the conditions used to effect the reaction between CO and hydrogen. Very high pressure reactions require only soluble rhodium, oxide of carbon (such as carbon monoxide) and hydrogen to form a desirable rhodium carbonyl complex.

Nitrogen Lewis bases used as promoters generally contain hydrogen and nitrogen atoms. They may also contain carbon and/or oxygen atoms. They may be organic or inorganic compounds. With respect to the organic compounds, the carbon atoms can be part of an acyclic and/or cyclic radical such as aliphatic, cycloaliphatic, aromatic (including fused and bridged) carbon radicals, and the like. Preferably, the organic Lewis bases contain from 2 to 60, most preferably 2 to 40 carbon atoms. The nitrogen atoms can be in the form of imino (—N═), amino, (—N—), nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic), carboxyl (—COH), carbonyloxy (—CO—), oxy (—O—), carbonyl (—C—), etc., all of said groups containing Lewis base oxygen atoms. In this respect, it is the "hydroxyl" oxygen in the —COH group and the "oxy" oxygen in the —CO— groups that are acting as Lewis base atoms. The organic Lewis bases may also contain other atoms and/or groups as substituents of the aforementioned radicals, such as alkyl, cycloalkyl, aryl, chloro, trialkylsilyl substituents.

Illustrative of organic aza-oxa Lewis bases are, for example, the alkanolamines, such as ethanolamine, diethanolamine, isopropanolamine, di-n-propanolamine, and the like; N,N-dimethylgylcine, N,N-diethylglycine, iminodiacetic acid, N-methyliminodiacetic acid; N-methyldiethanolamine, 2-hydroxypyridine, 2-4-dihydroxy pyridine, 2-methoxypridine, 2,6-dimethoxypyridine, 2-ethoxypyridine; lower alkyl substituted hydroxypyridines, such as 4-methyl-2-hydroxypyridine, 4-methyl-2,6-dihydroxypyridine, and the like; morpholine, substituted morpholines, such as 4-methylmorpholine, 4-phenylmorpholine; picolinic acid, methyl-substituted picolinic acid; nitrilotriacetic acid, 2,5-dicarboxypiperazine, N-(2-hydroxyethyl) iminodiacetic acid, ethylenediamine tetraacetic acid; 2,6-dicarboxypyridine; 8-hydroxyquinoline, 2-carboxyquinoline, cyclohexane-1,2-diamine -N,N,N',N-tetraacetic acid, the tetramethyl ester of ethylenediamine-tetraacetic acid, and the like.

Other Lewis base nitrogen containing compounds include organic and inorganic amines.

Illustrative of such inorganic amines are, e.g., ammonia, hydroxylamine, and hydrazine. Primary, secondary, or tertiary organic amines are promoters. This includes the mono- and polyamines (such as di, tri-, tetraamines, etc.) and those compounds in which the Lewis base nitrogen forms part of a ring structure as in pyridine, quinoline, pyrimidine, morpholine, hexamethylenetetraamine, and the like. In addition, any compounds capable of yielding an amino nitrogen under the reaction conditions of the present invention are promoters, as in the case of an aminde, such as formamide, cyanamide, and urea, or an oxime. Further illustrative of Lewis base nitrogen compounds are aliphatic amines such as methylamine, ethylamine, n-propylamine, isopropylamine, octylamine, dodecylamine, dimethylamine, diethylamine, diisoamylamine, methylethylamine, diisobutylamine, trimethylamine, methyldiethylamine, triisobutylamine, tridecylamine, and the like; aliphatic and aromatic di and polyamines such as 1,2-ethanediamine, 1,3-propanediamine, N,N,N',N'-tetramethylenediamine, N,N,N',N'-tetraethylenediamine, N,N,N',N'-tetra-n-propylethylenediamine, N,N,N',N'-tetrabutylethylenediamine, o-phenylenediamine, m-phenylenediamine, p-phenylenediamine, p-tolylenediamine, o-tolidene, N,N,N',N'-tetramethyl-p-phenylenediamine, N,N,N',N'-tetraethyl-4,4'-biphenyldiamine, and the like; aromatic amines such as aniline, 1-naphthylamine, 2-naphthylamine, p-toluidine, o-3-xylidine, p-2-xylidine, benzylamine, diphenylamine, dimethylaniline, diethylaniline, N-phenyl-1-naphthylamine, bis-(1,8)-dimethylaminonapthalene, and the like; alicyclic amines such as cyclohexylamine, dicyclohexylamine, and the like; heterocyclic amines such as piperidine; substituted piperidines such as 2-methylpiperidine, 3-methylpiperidine, 4-ethylpiperidine, and 3-phenylpiperidine, substituted pyridines such as 2-methylpyridine, 2-phenylpyridine, 2-methyl-4-ethylpyridine, 2,4,6-trimethylpyridine, 2-dodecyl- pyridine, 2-chloropyridine, and 2-(dimethylamino) pyridine; quinoline; substituted quniolines, such as 2-(dimethylamine)-6-methoxyquinoline; 4,5-phenanthroline; 1,8-phenanthroline; 1,5-phenanthroline; piperazine; substituted piperazines such as N-methylpiperazine, N-ethylpiperazine, 2-methyl-N-methyl- piperazine; 2,2'dipyridyl, methyl-substituted, 2,2-dipyridyl; ethyl-substituted 2,2'-dipyridyl; 4-triethylsilyl-2,2'-dipyridyl; 1,4-diazabicyclo[2.2.2]octane, methyl substituted, 1,4-diazabi- cyclo[2.2.2]octane, purine and the like.

The promoter provided is present in an amount which is equal to or greater than that amount, determined from the promoter's basicity, which achieved the optimum rate of formation of said alkane polyol at said correlated catalyst concentration, temperature and pressure of such reaction mixture as described in British Patent Specifications Nos. 1,565,978 and 1,565,979.

The concentration of the promoter will typically be within about 0.001 to about 10 molar. Obviously this range is definitive of the potential scatter of concentrations predicated on the varieties of promoter basicity available.

Salts are also provided in the homogeneous liquid phase reaction mixture. Suitable salts include any organic or inorganic salt which does not adversely affect the production of polyhydric alcohols. Experimental work suggest that any salt is beneficial as either a copromoter and/or in aiding in maintaining rhodium in solution during the reaction. Illustrative of the salts usefulness are the ammonium salts and the salts of the metals of Group I and Group II of the Periodic Table (Handbook of Chemistry and Physics—50th Edition) for instance the halide, hydroxide, alkoxide, phenoxide and carboxylate salts such as sodium fluoride, cesium fluoride, cesium p-methylsulfonylbenzoate ($CH_3SO_2C_6H_4COO$)Cs, rubidium acetate, magnesium acetate, strontium acetate ammonium formate, ammonium benzoate and the like. Preferred are the cesium, rubidium, potassium and ammonium salts.

Also useful are organic salts of the following formula:

$$R_4-\underset{\underset{R_3}{|}}{\overset{\overset{R_1}{|}}{N}}-R_2 \quad Y \qquad (I)$$

quartnenary ammonium salts

-continued

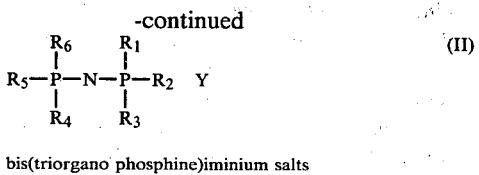

bis(triorgano phosphine)iminium salts wherein $R_1$ through $R_6$ in formulas (II) and (III) above are any organic radicals which do not adversely affect the production of polyhydric alcohols by reacting oxides of carbon with hydrogen in the presence of the aforedefined rhodium carbonyl complex, such as a straight or branched chain alkyl group, having from 1 to 20 carbon atoms in the alkyl chain, such as methyl, ethyl, n-propyl, isopropyl, n-butyl, octyl, 2-ethylhexyl, dodecyl, and the like; or a cycloaliphatic group including the monocyclic and bicyclic groups cyclopentyl, cyclohexyl, and bicyclo[2.2.1] heptyl groups, and the like or an aryl, alkylaryl, or aralkyl group such as phenyl, naphthyl, xylyl, tolyl, t-butylphenyl, benzyl, beta-phenylethyl, e-phenylpropyl and the like; or a functionally substituted alkyl such as beta-hydroxyethyl, ethoxymethyl, ethoxyethyl, phenoxyethyl, and the like or a polyalkylene ether group of the formula $(C_nH_{2n}O)_x$—OR wherein n has an average value from 1 to 4, x has an average value from 2 to about 150, and R may be hydrogen or alkyl of 1 to 12 carbon atoms. Illustrative of such polyalkylene ether groups are poly(oxyethylene), poly(oxypropylene), poly(oxyethyleneoxypropylene), poly(oxyethyleneoxybutylene), and the like. Y in formulas I and II above may be any anion which does not adversely affect the production of polyhydric alcohols in the practice of the present invention such as hydroxide; a halide, for instance fluoride, chloride, bromide and iodide; a carboxylate group, such as formate, acetate, propionate, and benzoate and the like; an alkoxide group such as methoxide, ethoxide, phenoxide, and the like; a functionally substituted alkoxide or phenoxide group such as methoxyethoxide, ethoxyethoxide, phenoxyethoxide and the like; a pyridinolate or quinolate group and others. Preferably Y in formulas I and II above is a carboxylate, most preferably formate, acetate and benzoate.

A suitable method for preparing the bis(triorganophosphine) iminium salts is disclosed in an article by Appel, R. and Hanas, A., appearing in Z. Anorg. u. Allg. Chem., 311, 290, (1961).

Other organic salts useful in the practice of the present invention include the quaternized heterocyclic amine salts such as the pyridinium, piperidinium, morpholinium, quinolinium salts and the like, e.g., N-ethylpyridinium fluoride, N-methylmorpholinium benzoate, N-phenylpiperidinium hydroxide, N,N'-dimethyl-2,2-bipyridinium acetate, and the like.

In addition, the anion of the above salt may be any of the Group VIII metal carbonyl anions. For example, if the Group VIII metal is rhodium suitable rhodium carbonyl anions include $[Rh_6(CO)_{15}]^{2-}$; $[Rh_6(CO)_{15}Y]^-$ wherein Y may be halogen, such as chlorine, bromine, or iodine, $[Rh_6(CO)_{15}(COOR'')]^-$ wherein $R''$ is lower alkyl or aryl such as methyl, ethyl, or phenyl; $[Rh_6(CO)_{14}]^{2-}$; $[Rh_7(CO)_{16}]^{3-}$; $[Rh_{12}(CO)_{30}]^{2-}$; $Rh_{13}(CO)_{24}H_3{}^{-2}$; and $Rh_{13}(CO)_{24}H_2{}^{-3}$.

The choice of extraction solvent will be dependent, in part, on the selection of the production solvent but in all cases, will be a polyhydric alcohol, which is a liquid at the process temperature, having at least four carbon atoms and at least 4 hydroxyl moieties. The term "extraction solvent" is employed herein to refer to a compound having at least four hydroxyl moieties and 4 carbon atoms. The extraction solvent preferably contains one hydroxyl group per carbon atom. Exemplary of such liquid polyhydric alcohols are: 1,2,3,4-tetrahydroxybutanes such as erythritol and threitol of the D, L and DL types and 1,2,3,4,5-pentahydroxypentanes such as ribitol, xylitol and arabitol of the D, L and DL types; 1,2,3,4,5,6-hexahydroxyhexane such as allitol, dulcitol, sorbitol of D, L and DL types; mannitol of D, L and DL type; iditol of the L and D type; and totitol of the D, L and DL type. (The letters, D, L and DL designate the arrangement of $H^+$ and $OH^-$ groups along the carbon chain). The preferred extraction solvents are those polyhydridric alcohols having at least 6 or 7 carbon atoms with 6 or 7, respectively, hydroxyl groups.

In the following examples the use of 18-Crown-6 as the production solvent and sorbitol as the extraction solvent provided for high retention of the rhodium catalyst by the production solvent. In fact, the concentration of rhodium catalyst in the production solvent was observed in many instances to be less than 50 ppm (by weight) based on the initial weight of rhodium, when 18-Crown-6 was the production solvent and sorbitol was the extraction solvent. Such retention of the rhodium catalyst by the production solvent is extremely advantageous in preventing the loss of the valuable rhodium catalyst and has not heretofore been reported for the polyhydric extraction solvents employed in the instant invention.

The extraction procedure involves any method which effects contact between the production solution and an amount of extraction solvent sufficient to remove a desired amount of alcohol product from the production solvent and retain an adequate amount of the rhodium values in the production solvent phase. The ratio extraction solvent to production solvent may range, on a volume basis, from about 0.01 to 100, though it is preferred to use a ratio of 0.1 to 10. In the preferred embodiment, the amount of extraction solvent is desirably sufficient to essentially remove the alcohol products, specifically ethylene glycol, to the extraction solvent phase and retain the rhodium values in a production solvent phase.

The extraction solvent may be admixed with the production solution after the reaction is run or, alternatively, the extraction solvent may be premixed and blended with the production solution prior to carrying out the reaction to form ethylene glycol and other products. According to the latter, the procedure involves the addition of the production solution and the extraction solvent to a vessel with agitation.

The extraction process may be effected at a temperature of at least 50° C. and generally at a temperature from about 50° C. to about 400° C., and preferably from about 50° C. to about 150° C. Pressures ranging from subatmospheric to superatmospheric pressures are suitably employed, e.g., 0.1 mm. Hg pressure to about 5000 atmospheres pressures are contemplated as employable.

Any of the known extraction procedures may be employed, such as mixing in a vessel with stirring followed by settling and decantation, or countercurrent extraction in which the extraction solvent is countercurrently fed with the production solution, or by extraction in a agitated column, and the like. When carrying out the process under low pressures, e.g., less than about 500 psig., the process is effected using any apparatus wherein mixing occurs such that products can be exchanged from the production solvent to the extraction solvent. Such procedures as mixing followed by settling and decantation, counter-current extraction and centrifugal extraction are exemplary of such extraction procedures. It is preferred to carry out the process as a counter-current extraction wherein a dispersed phase and a continuous phase wherein the extraction solvent is the continuous phase. The actual transfer of products being dependent, in part, on the molecular diffusivity, the degree of droplet oscillation, ratio of stream mass flows and the surface wetting properties of the extractor. The process may also be carried out as a high pressure process, although in such case the process will usually involve a pressure let-down step into a vapor liquid separator.

The actual process design, i.e., extraction scheme, will be dependent, in part, on the mode of reactor operation. The process may be carried out in a stripping reactor under process pressure, e.g., 15,000 psig at the process temperature. In such a process scheme any gas (carbon monoxide and hydrogen) dissolved in the extraction solvent phase during extraction may be recovered by a pressure letdown and a vapor-liquid separation. The recovered gas may then be recycled. Alternatively, the extraction process may be carried out in an adiabatic liquid overflow reactor. The adiabatic liquid overflow reactor differs from the stripping reactor, aforementioned, by containing a higher weight percent of production solvent in the liquid phase; 70 to 90 weight percent production solvent as compared to 40 to 60 weight percent production solvent being employed in the condensed liquid phase of a stripping reactor. The stripping reactor and the adiabatic liquid overflow reactor may also be employed in a "low pressure" extraction. When employed in such a low pressure extraction the dissolved gases in the production solvent are recovered prior to the extraction process. This may be done by conventional means such as by gas stripping and the like. In addition, low-boiling compounds such as methanol may desirably be recovered prior to carrying out the extraction process according to this invention.

The removed alcohol products may be isolated from the extraction solvent by fractional distillation.

EXAMPLE 1

The reactor solvent must form two liquid phases when mixed with the polyhydric extraction solvent. Experiments were carried out with a variety of polyhydric compounds in binary solutions with 18-Crown-6 ether, as the production solvent, to determine solubility levels of the extraction solvent in the production solvent and in the polyhydric layer. This was done by adding approximately 5 gms of a selected polyhydric to an equivalent weight of 18-Crown-6 ether, contained in a small tube. The two compounds were then thoroughly mixed and allowed to settle while holding the mixture at a temperature of 130° C. Samples of each phase were then withdrawn and analyzed by gas chromatography. The procedure was then repeated at 200° C.

TABLE I

| Extraction Solvent | Sorbitol[1] Layer | | 18-Crown-6 Layer[1] | | Melting Point (°C.)[2] |
|---|---|---|---|---|---|
| | 130° C. | 200° C. | 130° C. | 200° C. | |
| Erythritol (-meso) | 91.7 | 34.7 | 16.2 | 33.9 | 124 |
| Xylitol | 95.4 | 76.8 | 7.6 | 14.5 | 93–95 |
| Ribitol | 90.5 | 54.1 | 11.3 | 17.7 | 102 |
| Sorbitol | 100.0 | 83.5 | 1.9 | 7.8 | 93–97 |
| Mannitol | — | 39.9 | — | ~1.0 | 167 |

[1] values given as a weight percent based on total weight of layer
[2] of pure extraction solvent

EXAMPLE 2

A series of single stage contact experiments were carried out at varying weight ratios of sorbitol (as the extraction solvent) to the production solvent (See Table II). The production solvent was a synthesized mixture of ethylene glycol (2.0 wt. percent), glycerine (8.0 wt. percent), erythritol (3.0 wt. percent), xylitol (2.0 wt. percent) and 18-Crown-6 ether (85.0 wt. percent). The single stage contact experiments were carried out by adding and mixing about 5, 10 or 15 grams of sorbitol with about 15 grams of the synthesized mixture and then allowing the phases to settle at a temperature of 130° C. After a period of one hour, a sample of each phase was withdrawn and analyzed by gas chromatography.

The recovery of products was observed to increase as the number of carbon atoms in that product molecule increased, e.g., a greater percentage of glycerine was extracted as compared to ethylene glycol and a greater percentage of xylitol was extracted as compared to erythritol.

TABLE II

| Run | Wt. Ratio[4] | Glycol | K[2] | Glycerine | K | Erythritol | K | Xylitol | K | 18-C-6 | K | Sorbitol into[5] 18 Crown-6 |
|---|---|---|---|---|---|---|---|---|---|---|---|---|
| A | 0.961 | 69.7 | 1.96 | 73.5 | 3.86 | 75.8 | 6.55 | 86.2 | 76 | 3.1 | 0.292 | 5.68 |
| B | 0.5556 | 63.2 | 2.32 | 69.6 | 3.79 | 72.9 | 7.826 | 86.0 | 6.925 | 1.1 | 0.017 | 6.67 |
| C | 0.302 | 53.5 | 2.52 | 63.8 | 6.05 | 64.7 | 7.55 | 82.6 | 8.68 | 0.84 | 0.0215 | 16.0 |

Recovery[1,3]

[1] The original mixture comprised ethylene glycol (2 wt. percent); glycerine (8.0 wt. percent) erythritol (3.0 wt. percent); xylitol (2.0 wt. percent); and 18-Crown-6 (85.0 wt. percent).
[2] Where $K = \frac{\text{wt. percent of polyhydric in extract phase (sorbitol phase)}}{\text{wt. percent of polyhydric in raffinate phase (non-sorbitol phase)}}$
[3] Percent recovered into extraction solvent phase.
[4] Weight ratio of extraction solvent to production solvent.
[5] As a weight percent of total extraction solvent.

EXAMPLE 3

Single stage extractions (9 in total) were made using production mixtures, as indicated in Table III, with sorbitol as the extraction solvent. The experimental procedure was the same as in Example 2.

The percent recovery of the various components of the production solvent was generally above about 70 percent by weight and the amount of 18-Crown-6 ether present in the extraction solvent was generally below about 5 percent of the total 18-Crown-6 ether employed. The results of these extractions are set forth in Table III.

EXAMPLE 4

A one inch diameter pulsed plate extractor, i.e. a Karr (TM) extractor, was used to recover polyhydric products prepared by carrying out the process as described in U.S. Pat. No. 3,833,634 with sorbitol as the extraction solvent. A total of five runs were made and in each run the recovery of ethylene glycol and glycerine was above 80 percent from feed streams containing about 20 wt. percent polyhydrics. The results of these runs are set forth in Table IV.

EXAMPLE 5

Four runs were carried out in which sorbitol, 18-Crown-6 ether, rhodium acetylacetonate, potassium bicarbonate and N-methylmorpholine were charged to a high pressure stirred autoclave according to the procedure set forth in U.S. Pat. No. 3,833,634, incorporated herein. A equimolar mixture of carbon monoxide and hydrogen was then introduced into the autoclave until the pressure about reached 15,000 psig. The temperature was then raised to 250° C. Under such conditions, polyhydric products are formed. As carbon monoxide and hydrogen are consumed, as indicated by a drop in the pressure in the autoclave, further gas is introduced into the reactor to maintain the 15,000 psig reaction pressure. After a period of about one hour, the reactor was cooled to 130° C. at which point two phases were formed in the reactor. The stirrer was shut off after a period of 15 minutes and the phases are allowed to settle for 1 hour. At the end of this period, five 15 cc high pressure liquid samples are withdrawn from the base of the autoclave for analysis.

The recovery of ethylene glycol in each run varied from about 54 to about 68 percent while the recovery of glycerine varied from about 75 to about 84 percent for those runs where the weight ratio of sorbitol to 18-Crown-6 ether had an average value of at least about 1.12, see (Table V).

EXAMPLE 6

Example 6 was carried out by employing a mixture of sorbitol and 18-Crown-6 (33 milliliters 18-Crown-6; 42.5 grams of Sorbitol; 0.78 mmoles $KHCO_3$; 3.0 mmoles $Rh(CO)_2$*AcAc; 6.0 mmoles nMM) the production solvent. After 6000 psig of gas was taken up, at 250° C., the reactor was cooled to 130° C. while maintained at the reaction pressure. The reaction rate to ethylene glycol was 1.01 gram moles/liter/hour. Samples were taken from the reactor and were observed to form two phases. The two phases were analyzed with the lower sorbitol layer containing 68 percent by weight of the ethylene glycol and 75 percent by weight of the glycerine. The remaining ethylene glycol and glycerine were in the upper, 18-Crown-6 layer. Decomposition products, believed to come from sorbitol, were observed by vapor pressure chromatography.

*AcAc=Acetonylacetonate

EXAMPLE 7

Three runs (A, B, and C) were carried out according to the process of U.S. Pat. No. 3,833,634 using a sorbitol/18-crown-6ether mixture (53 wt. percent sorbitol). After 6000 psig of a carbon monoxide and hydrogen gas (1:1) was taken up at 250° C., the reactor was cooled to 130° C. but kept under pressure (~12,000 psig). Samples taken from the reactor at these conditions showed that two phases were present. The sorbitol fraction contained ethylene glycol and glycerine while there was a high retention of rhodium catalyst by the 18-Crown-6 ether phase. The following was observed:

| Run | Fraction of Products in Sorbitol Layer EG | Glycerine | Sorbitol[4] | 18-Crown-6[4] | Selectivity | Rhodium[5] in 18-C-6 Layer |
| --- | --- | --- | --- | --- | --- | --- |
| A[1] | .546 | .756[1] | — | — | — | — |
| B | .643 | .793[2] | 5251 | 102 | 51 | .985 |
| C | .623 | .839[2] | 4326 | 59 | 73 | .983 |

[1]42 gms sorbitol, 33 ml 18-C-6, 3.0 mm $Rh(CO)_2$ AcAc 0.78 mm $KHCO_3$, 6.0 mm n-methyl morpholine. (mm = millimole)
[2]56 gms sorbitol, 44 ml 18-C-6, 4.0 mm $Rh(CO)_2$ AcAc 1.04 mm $KHCO_3$, 8.0 mm n-methyl morpholine.
[3]at 130° C. and 12,000 psig.
[4]parts per million of rhodium in the sorbitol layer and the 18-Crown-6 layer.
[5]rhodium in 18-Crown-6 layer (top layer) given as a weight percent of total rhodium employed.

TABLE III

| Extractions[1] | Solvent/Feed[2] | Tetraglyme[5] | Glycol[3] | Glycerine[3] | Erythritol[5] | Xylitol[3] | 18-Crown-6[3] | Sorbitol[4] |
| --- | --- | --- | --- | --- | --- | --- | --- | --- |
| 1 | — | 3.8 | 11.1 | 6.9 | 2.6 | 1.8 | 73.8 | — |
| A | 0.994 | — | 75.8 | 68.8 | — | ~100 | 4.2 | 8.7 |
| B | 0.623 | — | 67.2 | 73.4 | — | 94.5 | 2.6 | 14.0 |
| C | 0.302 | — | 54.5 | 58.4 | — | 92.1 | 1.7 | 22.1 |
| 2 | — | 2.7 | 7.5 | 7.3 | 2.8 | 1.9 | 77.8 | — |
| D | 1.002 | — | 81.4 | 86.7 | — | 97.3 | 2.6 | — |
| E | 0.603 | — | 71.9 | 75.8 | — | ~100 | 3.4 | — |
| 3 | — | 3.6 | 4.3 | 8.1 | 2.9 | 1.9 | 79.2 | — |
| F | 0.972 | — | 78.3 | 85.3 | — | ~100 | 2.0 | — |
| G | 0.594 | — | 74.9 | 71.4 | — | ~100 | 3.1 | — |
| 4 | — | 3.1 | 18.0 | 8.0 | — | 3.1 | 67.8 | — |
| H | 0.656 | — | 82.5 | 80.1 | — | 87.5 | 1.7 | 8.3 |
| I | 0.322 | — | 81.4 | 81.5 | — | 89.5 | 3.6 | 8.3 |

[1]the feed composition for extractions A-I are set forth immediately preceding the extractions to which they correspond, e.g. mixture 1 was the mixture employed in extractions A, B and C. Feed composition was product of reaction of 15 mm RhAcAc, 0.375 mm CsBz, 3.0 mm nMM after 6000 psig of CO and $H_2$ was taken up at 250° C. and 15000 psig. To this mixture was added additional quantities of reaction products as required for analysis and the values reported herein relate to the combined mixture.
[2]weight ratio
[3]percent recovery into extraction solvent phase
[4]percent transfer of sorbitol into production solvent phase
[5]the analysis by gas chromatography did not differentiate between tetraglyme and erythritol

TABLE IV

| Run[3] | Strokes/min | Products in Feed[2] Inlet | Outlet | 18-C-6[1] | Sorbitol[1] | Recovery[4] |
| --- | --- | --- | --- | --- | --- | --- |
| 1 | 120 | 18.3 | 2.01 | 900(d) | 1800 | 89.0 |
| 2 | 120 | 18.3 | 1.42 | 1860(d) | 1500 | 92.2 |
| 3 | 140 | 15.0 | 0.55 | 1860(d) | 1440 | 96.3 |
| 4 | 140 | 10.1 | 0.82 | 1860(d) | 960 | 91.9 |

TABLE IV-continued

| 5 | 140 | 13.3 | 3.45 | 1860 | 900(d) | 74.1 |

[d] designates a dispersed phase; cubic centimeters/min; 18-C-6 = 18-Crown-6.
[2] Concentration as a weight percent based on total feed weight
[3] Feed compositions wt %

| | Glycol | Glyc-erine | Xylitol | Tetra-glyme | 18-C-6 | Sor-bitol |
|---|---|---|---|---|---|---|
| Run 1 and 2 | 11.5 | 6.85 | — | 1.32 | 80.33 | — |
| Run 3 | 15.01 | — | — | — | 84.99 | — |
| Run 4 | 3.12 | 5.61 | 1.38 | 1.58 | 84.51 | 3.80 |
| Run 5 | 2.82 | 9.73 | 0.67 | 2.10 | 83.77 | 0.91 |

[4] Percent recovery based on total weight product in the feed.

TABLE V[1]

| Run | Recovery[2] | |
|---|---|---|
| | Ethylene Glycol | Glycerine |
| 1 | 68.0 | 74.5 |
| 2 | 54.6 | 75.6 |
| 3 | 64.3 | 79.3 |
| 4 | 62.3 | 83.9 |

[1] The following reaction mixture was employed for runs 1-4:

| Run | 18-Crown-6 Ether(ml) | Sorbitol (gms) | KHCO$_3$ (mmoles) | Rh(AcAc)$_2$ (mmoles) | nMM (mmoles) |
|---|---|---|---|---|---|
| 1 | 33 | 42.5 | 0.78 | 3.0 | 6.00 |
| 2 | 33 | 42.5 | 0.78 | 3.0 | 6.00 |
| 3 | 44 | 56.6 | 1.04 | 4.0 | 8.00 |
| 4 | 44 | 56.6 | 1.04 | 4.0 | 8.00 |

(KHCO$_3$ = potassium bicarbonate; RhAcAc = rhodium acetylacetonates; nMM = n-methyl morpholine; and mmoles = millimoles)
[2] recovery given as a weight percent.

EXAMPLES 8-12

Five single stage extractions were carried out according to the procedure of Example 2. During the extraction process one or more samples were taken for each example of the equilibrated layers and analyzed for rhodium. The rhodium concentration for said samples in the sorbitol phase and 18-Crown-6 phase was as follows for each sample of each example (see Table VI):

TABLE VI

| Example | Sorbitol Phase (ppm) | 18-Crown-6 Phase (ppm) |
|---|---|---|
| 8 | 167 | 685 |
| 9 | 52;167;90 | 1035;1006;969 |
| 10 | 587;313 | 2168;2973 |
| 11 | 176;156 | 1370;1357 |
| 12 | 20;36;25 | 2037;1850;1647 |

[1] Examples 8-12 were carried out at 250° C. except example 8 which was at 270° C., and under a pressure of 15,000 psig. The following amounts of rhodium, promoters and amine were employed in 75 milliliters of 18-Crown-6:

| Example | Rhodium (millimole) | Promoter(millimole) | nMM$^a$ (millimole) |
|---|---|---|---|
| 8 | 1.5 | Cesium Benzoate (0.375) | 3.0 |
| 9 | 1.5 | Cesium Benzoate (0.375) | 4.0 |
| 10 | 3.0 | Potassium Benzoate (0.28) | 6.0 |
| 11 | 1.5 | Potassium Benzoate (0.75) | — |
| 12 | 3.0 | Potassium Benzoate (0.56) | 6.0 |

$^a$nMM = n-methyl morpholine

EXAMPLES 13-15

The examples 13-15 were carried out in a stirred autoclave in which 50 gms of sorbitol were contacted with 50 gms of production mixture for a period of 15 minutes at 135° C. and at the designated carbon monoxide pressure. The mixture was then allowed to settle with stirrer off, in order to remove samples of either layer. Example 15 was carried out under a pressure of 15 psig (1:1 of H$_2$:CO), example 14 was carried out under a pressure of 500 psig (CO atmosphere), and example 15 was carried out under a pressure of 15 psig (CO). The concentration in the sorbitol and 18-Crown-6 layers and the selectivity of the layers are reported in Table VII.

TABLE VII

| Example[4] | Sorbitol[1] (ppm) | 18-Crown-6[1] (ppm) | Selectivity |
|---|---|---|---|
| 13[2] | 14.5 | 7173 | 495 |
| 14[3] | 4.8 | 1394 | 290 |
| 15 | 29.5 | 948 | 32 |

[1] ppm = parts per million of rhodium in phase
[2] production solvent comprised a sorbitol/18-Crown-6 mixture
[3] equal amounts of extraction solvent and production solvent contacted
[4] Production solvent; 75 ml of 18-Crown-6, 1.5 mm RhAcAc, 0.375 mmole CsBz, 30 mmole nMM. reacted at 15000 psig until 6000 psig of uptake at 250° C.

EXAMPLES 16-22

Samples 16-22 were carried out according to the procedure employed in examples 13 to 15 except that a pressure of carbon monoxide was employed as indicated in Table VIII.

TABLE VIII

| Example | Pressure[1] | Sorbitol[5] | 18-Crown-6[5] | Selectivity |
|---|---|---|---|---|
| 16[2] | 500 | 6.7 | 2569[6] | 383 |
| 17 | 15 | 15.4 | 5973 | 388 |
| 18[3] | 500 | 41.3 | 2232[6] | 54 |
| 19 | 15 | 7.8 | 6479 | 829 |
| 20[4] | 500 | 6.2 | 1005 | 162 |
| 21 | 250 | 5.3 | 944 | 178 |
| 22 | 15 | 12.4 | 513[6] | 41 |

[1] Pressure of carbon monoxide in psia
[2] The production solvent was the same in examples 16 and 17
[3] The production solvent was the same in examples 18 and 19
[4] The production solvent was the same in examples 20, 21 and 22
[5] Reported in parts per million (ppm) of rhodium
[6] Precipitation of rhodium occurred

What is claimed is:

1. A process for separating alkane polyol from a liquid phase homogeneous mixture obtained from a homogeneous liquid phase reaction of oxides of carbon and hydrogen to produce alkane polyol, said liquid phase homogeneous mixture comprising alkane polyol, production solvent and catalyst comprising rhodium, ruthenium or cobalt as the carbonyl complex, wherein said production solvent is a solvent for rhodium, ruthenium or cobalt of the catalyst, said process comprising:
   (a) extracting at a temperature of at least about 50° C., alkane polyol from said liquid phase homogeneous mixture by contact with an extraction solvent of polyhydric alcohol having at least four carbon atoms and at least four hydroxyl groups, such that two liquid phases are formed, one phase containing the greater concentration of alkane polyol and extraction solvent and the other phase containing the greater concentration of production solvent and the greater portion of rhodium, ruthenium or cobalt of the catalyst,
   (b) separating phases, and
   (c) recovering alkane polyol from the extraction solvent-containing phase.

2. The process of claim 1 wherein the concentration of rhodium, ruthenium or cobalt of the catalyst in the extraction solvent-containing phase is less than 50 ppm.

3. The process of claim 1 wherein said production solvent also contains monohydric alcohols.

4. The process of claim 1 wherein said extraction solvent has one hydroxyl per carbon atom.

5. The process of claim 2 wherein said extraction solvent is sorbitol.

6. The process of claim 1 wherein said production solvent is a crown ether.

7. The process of claim 6 wherein the crown ether is 18-Crown-6.

8. The process of claim 1 wherein the process is carried out in the presence of a carbon monoxide-containing gas.

9. The process of claim 8 wherein hydrogen is present.

10. The process of claim 1 wherein rhodium is contained in the production solvent.

11. The process of claim 1 wherein ruthenium is contained in the production solvent.

12. The process of claim 1 wherein cobalt is contained in the production solvent.

13. The process of claim 10 wherein the alkane polyol comprise ethylene glycol.

* * * * *